(12) United States Patent
Ugawa et al.

(10) Patent No.: US 11,598,712 B2
(45) Date of Patent: Mar. 7, 2023

(54) SYSTEM AND METHOD FOR CELL EVALUATION, AND CELL EVALUATION PROGRAM

(71) Applicants: THINKCYTE, INC., Tokyo (JP); The University of Tokyo, Tokyo (JP)

(72) Inventors: Masashi Ugawa, Tokyo (JP); Yoko Kawamura, Tokyo (JP); Sadao Ota, Tokyo (JP)

(73) Assignees: THINKCYTE, INC., Tokyo (JP); THE UNIVERSITY OF TOKYO, Tokyo (JP)

( * ) Notice: Subject to any disclaimer, the term of this patent is extended or adjusted under 35 U.S.C. 154(b) by 699 days.

(21) Appl. No.: 16/610,481

(22) PCT Filed: May 2, 2018

(86) PCT No.: PCT/JP2018/017499
§ 371 (c)(1),
(2) Date: Nov. 1, 2019

(87) PCT Pub. No.: WO2018/203568
PCT Pub. Date: Nov. 8, 2018

(65) Prior Publication Data
US 2020/0150022 A1    May 14, 2020

(30) Foreign Application Priority Data
May 2, 2017    (JP) .............................. JP2017-091957

(51) Int. Cl.
*G01N 15/14*    (2006.01)
*G01N 15/10*    (2006.01)

(52) U.S. Cl.
CPC ..... *G01N 15/1429* (2013.01); *G01N 15/1475* (2013.01); *G01N 2015/1006* (2013.01)

(58) Field of Classification Search
CPC .......... G01N 15/1429; G01N 15/1475; G01N 2015/1006; G01N 15/147; G01N 33/4833;
(Continued)

(56) References Cited

U.S. PATENT DOCUMENTS

| 6,249,341 | B1 | 6/2001 | Basiji et al. |
| 8,767,212 | B2 | 7/2014 | Kanda et al. |

(Continued)

FOREIGN PATENT DOCUMENTS

| EP | 3222997 A1 | 9/2017 |
| EP | 3275993 A1 | 1/2018 |

(Continued)

OTHER PUBLICATIONS

International Search Report (ISR) dated Jul. 31, 2018 (and English translation thereof), issued in International Application No. PCT/JP2018/017499.

(Continued)

*Primary Examiner* — Roy M Punnoose
(74) *Attorney, Agent, or Firm* — Holtz, Holtz & Volek PC

(57) ABSTRACT

A cell evaluation system includes physical measurement unit, a database, and evaluation unit. The evaluation unit refers to a relevance stored in the database, searches reference measurement information based on measurement information of a cell newly measured via the physical measurement unit, and evaluates the cell with biological measurement information associated with the searched reference measurement information.

10 Claims, 13 Drawing Sheets

(58) Field of Classification Search
CPC ...... G01N 33/483; G16B 40/20; G16B 40/30; G16B 40/10; C12M 1/34; G06T 1/00; G06T 7/00
See application file for complete search history.

(56) References Cited

U.S. PATENT DOCUMENTS

| | | | |
|---|---|---|---|
| 9,823,457 B2* | 11/2017 | Li | ........................ G02B 21/367 |
| 2011/0176127 A1 | 7/2011 | Kanda et al. | |
| 2015/0192767 A1* | 7/2015 | Li | ........................ G02B 21/367 |
| | | | 359/372 |
| 2017/0254741 A1 | 9/2017 | Suganuma et al. | |
| 2018/0080918 A1* | 3/2018 | Kato | ........................ C12M 1/34 |

FOREIGN PATENT DOCUMENTS

| | | |
|---|---|---|
| JP | 5534214 B2 | 5/2014 |
| JP | 2016189702 A | 11/2016 |
| WO | 2016080442 A1 | 5/2016 |
| WO | 2016158962 A1 | 10/2016 |
| WO | 2017073737 A1 | 5/2017 |

OTHER PUBLICATIONS

Written Opinion of the International Searching Authority dated Jul. 31, 2018 issued in International Application No. PCT/JP2018/017499.

* cited by examiner

FIG. 6
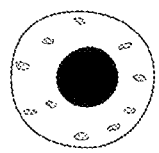 
IMAGE A OF REFERENCE
MEASUREMENT INFORMATION
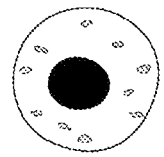 
IMAGE B OF REFERENCE
MEASUREMENT INFORMATION
⋮ ⋮
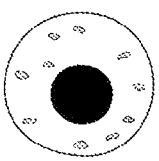 
IMAGE K OF REFERENCE
MEASUREMENT INFORMATION

TIME

SYSTEM AND METHOD FOR CELL EVALUATION, AND CELL EVALUATION PROGRAM

TECHNICAL FIELD

The present invention relates to a system and a method for cell evaluation, and a cell evaluation program appropriate for physically measuring one or more cells in a cell group to automatically evaluate the cells.

BACKGROUND ART

The smallest unit that constitutes an organism is a cell. Conventionally, various clarifications on functions, structures, forms, and the like of the organism have been carried out only for cell groups, but not carried out for the unit of individual cell constituting them.

However, recently, it has been found that gene expression is different for each cell even in a cell type having similar phenotype in a cancer tissue and the like. Therefore, instead of carrying out the various clarifications on a cell group basis, it is necessary to perform analyses on an individual cell basis.

As a cell measurement technique for such analysis with one cell (single cell), there has been proposed a flow cytometry method. The flow cytometry method is a technique where individual cells are dispersed in a fluid, and the fluid is finely flown down to be optically analyzed, and an apparatus using this technique is referred to as a flow cytometer. In the flow cytometry method, an observation target can be evaluated by irradiating microparticles such as cells as the observation targets with an excitation light while flowing down the microparticles through a flow passage at a high speed to obtain a total amount of a fluorescence intensity and/or scattered light emitted from the individual cells. The use of the flow cytometry method allows the analysis of the single cell with a very high throughput. Patent Document 1 discloses a flow cytometer and a flow cytometry method using the flow cytometer.

As a method for observing the phenotype of the individual cell in more detail, there has been known a fluorescence microscope and an imaging cytometer. These observation methods can obtain not only one-dimensional information such as the total amount of the fluorescence intensity and/or the scattered light emitted from the observation target, but also two-dimensional or three-dimensional morphological information. Meanwhile, different from the flow cytometer, because the observation target does not move, it is difficult to perform the single cell analysis in large scale with high throughput in these observation methods. In this respect, there has been known imaging flow cytometers that can take an image of the cell morphology information at high speed with a throughput equivalent to that of conventional flow cytometers (for example, see Patent Document 2), and the cell phenotype can be evaluated with two-dimensional or three-dimensional space information including fluorescent cell images. This ensures dramatical increase in the amount of information available for cell analysis while keeping the throughput of the existing flow cytometry method, and thus ensuring the improved quality and quantity in the cell phenotype analysis.

Furthermore, for effective use of the enormous volume of the cell morphology information generated by the imaging flow cytometer, there has been proposed a method where machine learning is used for the cell morphology information to evaluate and classify the cell (for example, see Patent Document 3). Specifically, there has been a method using, for example, a supervised machine learning where correct-information (teacher data) is provided in advance to configure a classifier and then the provided cell information is evaluated and classified, and an unsupervised machine learning where the provided cell information is evaluated and classified without the correct-information provided in advance.

Patent Document 1: Japanese Patent No. 5534214
Patent Document 2: U.S. Pat. No. 6,249,341
Patent Document 3: Japanese Patent Application No. 2015-212356 (Published as WO 2017/073737)

DISCLOSURE OF THE INVENTION

Problems to be Solved by the Invention

However, in the case where the supervised machine learning is used, the teacher giving a correct answer is a human, and the result of subjective evaluation and classification of the cell made by the human is used as the teacher data. Therefore, there has been a problem in that the information including the cell morphology information obtained by the physical measurement means can be classified and evaluated only in a range where the human can determine the difference, and the bias of each individual cannot be removed. In the unsupervised machine learning, while the classification and the evaluation can be automatically performed without the subjective determination by the human, with what determination criterion the machine performs the classification and the evaluation cannot be explained, and whether the results of the classification and the evaluation are biologically meaningful or not cannot have been explained.

When the conventional biological measurement method, such as a next-generation DNA/RNA sequencing, a polymerase chain reaction (PCR), and a DNA microarray, is used, the classification and the evaluation of the cell can be accurately performed because they are performed based on biochemical and molecular biological information such as cellular nucleic acid, protein, and metabolism. However, these biological measurement methods are much more expensive compared with the physical measurement methods, and a problem arises in that the throughput is too late to perform the single cell analysis in large scale.

Therefore, the present invention has been made in consideration of the above-described problems, and an object of the present invention is to provide a system and a method for cell evaluation and a cell evaluation program configured such that evaluation and classification of the cells are automatically performed at a high speed with accuracy and ease by physically measuring one or more cells in a cell group and giving answers to the biological measurement information.

Solutions to the Problems

To solve the above-described problems, the inventors invented a system and a method for cell evaluation, and a cell evaluation program where a relevance in three or more levels with reference measurement information is referred, the reference measurement information is searched based on newly measured measurement information of a cell, and the cell is evaluated with biological measurement information associated with the searched reference measurement information, the relevance in three or more levels being previously stored in a database, each piece of the reference measurement information being associated with the biological measurement information, and the biological measurement information being information to evaluate the cells.

That is, the cell evaluation system according to the present invention is a cell evaluation system that physically measures one or more cells in a cell group to evaluate the cells, and the cell evaluation system includes physical measurement means, a database, and evaluation means. The physical measurement means physically measures the one or more cells. The database previously stores a relevance in three or more levels between measurement information measured by the physical measurement means and reference measurement information. Each piece of the reference measurement information is associated with biological measurement information. The biological measurement information is information to evaluate the cells. The evaluation means refers to the relevance stored in the database, searches the reference measurement information based on the measurement information of a cell which is newly obtained via the physical measurement means, and evaluates the cells with the biological measurement information associated with the searched reference measurement information.

The cell evaluation system according to the present invention is a cell evaluation system that physically measures one or more cells in a cell group to evaluate the cells, and the cell evaluation system includes physical measurement means, a database, and evaluation means. The physical measurement means physically measures the one or more cells. The database preliminarily stores a relevance of three or more levels between measurement information and biological measurement information. The measurement information is measured by the physical measurement means. The biological measurement information is information to evaluate the cells. The evaluation means refers to the relevance stored in the database, searches the biological measurement information based on measurement information of a cell newly measured via the physical measurement means, and evaluates the cell with the searched biological measurement information.

The cell evaluation system to which the present invention is applied is a cell evaluation system that physically measures one or more cells in a cell group to evaluate the cells, and the cell evaluation system includes physical measurement means, a database, and evaluation means. The physical measurement means performs a physical measurement by irradiating a cell group as a measurement object flowing down in a flow passage with a structured excitation light or a structured illuminating light, individually interacting cells with the excitation light or the illuminating light in time series, and mapping optical space information of the cells in time series waveforms. The database previously stores a relevance in three or more levels between the measurement information measured by the physical measurement means and cell identification information. The evaluation means refers to the relevance stored in the database, and identifies the cell identification information based on the measurement information of a cell newly obtained via the physical measurement means.

The cell evaluation method according to the present invention is a cell evaluation method that physically measures one or more cells in a cell group to evaluate the cells, and the cell evaluation method includes: previously storing a relevance in three or more levels between physically measured measurement information and reference measurement information in a database, each piece of the reference measurement information being associated with biological measurement information, and the biological measurement information being information to evaluate the cells; and referring to the relevance stored in the database, searching the reference measurement information based on newly obtained measurement information of a cell, and evaluating the cells with the biological measurement information associated with the searched reference measurement information.

The cell evaluation method according to the present invention is a cell evaluation method that physically measures one or more cells in a cell group to evaluate the cells, and the cell evaluation method includes: performing a physical measurement by irradiating a cell group as a measurement object flowing down in a flow passage with a structured excitation light or a structured illuminating light, individually interacting cells with the excitation light in time series, and mapping optical space information of the cells in time series waveforms; previously storing a relevance in three or more levels between the measured measurement information and cell identification information in a database; and performing an evaluation by referring to the relevance stored in the database to identify the cell identification information based on newly measured measurement information of a cell.

The cell evaluation program according to the present invention is a cell evaluation program to physically measure one or more cells in a cell group to evaluate the cells, and the cell evaluation program causing a computer to execute: referring a relevance in three or more levels to reference measurement information, searching the reference measurement information based on newly measured measurement information of a cell, and evaluating the cells the biological measurement information associated with the searched reference measurement information, the relevance in three or more levels being preliminarily stored in a database, each piece of the reference measurement information being associated with the biological measurement information, and the biological measurement information being information to evaluate the cells.

The cell evaluation program according to the present invention is a cell evaluation program to physically measure one or more cells in a cell group to evaluate the cells, and the cell evaluation program causing a computer to execute: performing a physical measurement by irradiating a cell group as a measurement object flowing down in a flow passage with a structured excitation light or a structured illuminating light, individually interacting cells with the excitation light in time series, and mapping optical space information of the cells in time series waveforms; previously storing a relevance in three or more levels between the measured measurement information and cell identification information in a database; and performing an evaluation by referring to the relevance stored in the database to identify the cell identification information based on newly measured measurement information of a cell.

Effects of the Invention

The cell evaluation system to which the present invention is applied can select the reference measurement information from the measurement information of the cell newly obtained via the imaging flow cytometer analyzer by referring to the above-described relevance, further determine the cell type from this reference measurement information via the biological measurement information, and eventually evaluate the cell. Moreover, the cell evaluation system to which the present invention is applied can automatically perform these evaluation operations without human intervention. This ensures a high-speed and accurate classification and evaluation of the cell information on the basis of the newly obtained measurement information of the cell, not based on the subjective determination by an observer but based on the biologically correct correct-information. Since the identification of the cell type of each of the individual cells made by the imaging flow cytometer analyzer with imaging flow cytometry technology can be automatically carried out, and the cell evaluation is successfully achieved in the ultimate, the enormous amount of information generated by this technology can be effectively utilized.

BRIEF DESCRIPTION OF THE DRAWINGS

FIG. 6 is a drawing illustrating an example of immediate identification of a cell type via biological measurement information which is made through the process of selecting the reference measurement information.

DESCRIPTION OF PREFERRED EMBODIMENTS

The following describes a cell evaluation system to which the present invention is applied in detail with reference to the drawings.

First Embodiment

Figure 1:
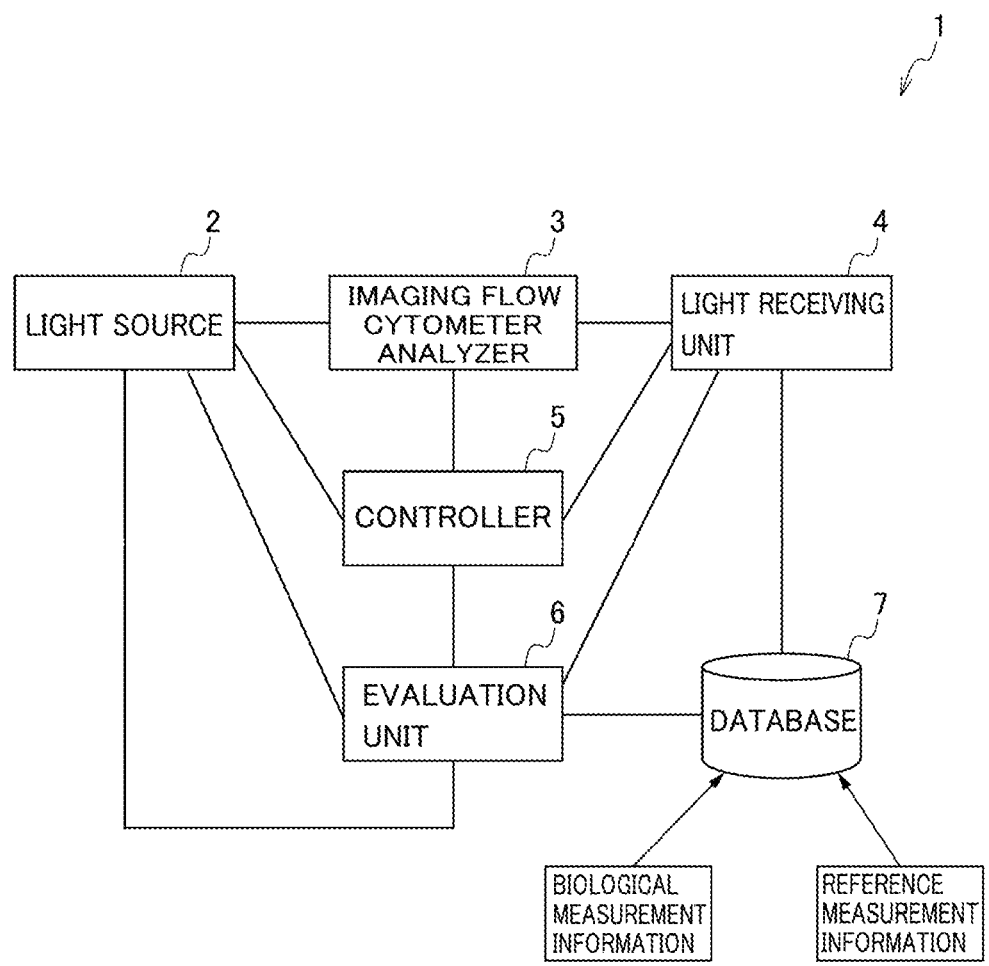
FIG. 1 is a block configuration diagram of a cell evaluation system in the first embodiment.

FIG. 1 illustrates the first embodiment of a cell evaluation system 1 to which the present invention is applied. The cell evaluation system 1 includes a light source 2, an imaging flow cytometer analyzer 3 irradiated with a light from the light source 2, a light receiving unit 4 that receives light information from the imaging flow cytometer analyzer 3, a controller 5 connected to each of the light source 2, the imaging flow cytometer analyzer 3, and the light receiving unit 4, an evaluation unit 6 connected to each of the light source 2, the light receiving unit 4, and the controller 5, and a database 7 connected to the evaluation unit 6 and the light receiving unit 4.

The light source 2 emits the light necessary for an analysis in the imaging flow cytometer analyzer 3. The imaging flow cytometer analyzer 3 disperses individual cells in a fluid, finely flows down the fluid to optically analyze the cell, and obtain the cell morphological information, based on an imaging flow cytometry method. The details of the imaging flow cytometer analyzer 3 will be described later in detail.

The light receiving unit 4 includes a sensor for receiving the light information obtained through the imaging flow cytometry method by the imaging flow cytometer analyzer 3. The controller 5 assumes a role of a central control unit to control the light source 2, the imaging flow cytometer analyzer 3, the light receiving unit 4, and the evaluation unit 6. The controller 5 comprises, for example, a personal computer (PC), a mobile terminal, a smart phone, a wearable device, and a tablet type terminal.

The evaluation unit 6 obtains the light information obtained from the light receiving unit 4, and further refers to information stored in the database, thus evaluating the cells flowing down in the imaging flow cytometer. In this cell evaluation, identification of cell type, function and characteristics of a cell, and the like are included. As with the controller 5, the evaluation unit 6 comprises, for example, a PC, a mobile terminal, a smart phone, a wearable device, and a tablet type terminal. Incidentally, the evaluation unit 6 may be configured as a device integrated with the above-described controller 5. The database 7 includes a hard disk and the like to store information necessary for the cell evaluation by the above-described evaluation unit 6.

Figure 2:
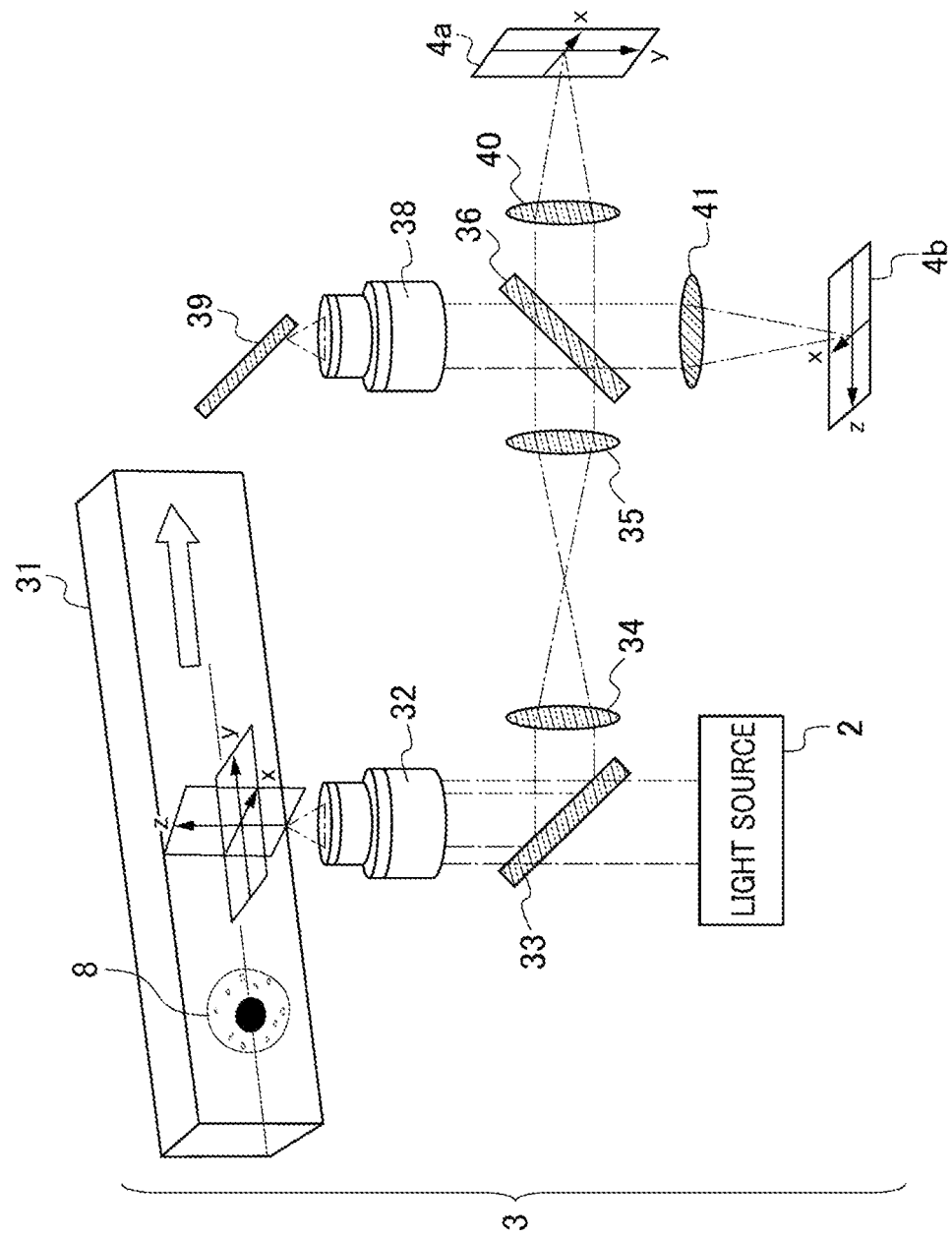
FIG. 2 is a drawing illustrating a detailed configuration of an imaging flow cytometer analyzer.

FIG. 2 illustrates the detailed configuration of the imaging flow cytometer analyzer 3. The imaging flow cytometer analyzer 3 obtains a three-dimensional fluorescent image for an individual cell 8 flowing in a flow passage 31. The imaging flow cytometer analyzer 3 includes a first objective lens 32, a first beam splitter 33, a first lens 34, a second lens 35, a second beam splitter 36, a second objective lens 38, a mirror 39, a third lens 40, and a fourth lens 41.

The first objective lens 32 focuses the light supplied from the light source 2 into the flow passage 31, and collects a feedback light reflected by the flow passage 31 to send this to the first beam splitter 33. The first beam splitter 33 has a function to directly pass the light emitted from the light source 2 and reflect the feedback light from the first objective lens 32. The first lens 34 and the second lens 35 adjust a focus position, a spot diameter, and the like of the feedback light reflected by the first beam splitter 33. The second beam splitter 36 reflects a part of the feedback light passed through the second lens 35 toward the second objective lens 38 while directly passing a part of the feedback light. The second objective lens 38 guides the feedback light reflected by the second beam splitter 36 to the mirror 39, while collecting the feedback light reflected by the mirror 39 and passing this through the second beam splitter 36 to guide to the fourth lens 41. The mirror 39 reflects the feedback light from the second objective lens 38. The third lens 40 collects the feedback light passed through the second beam splitter 36 to form an image on a first light receiving sensor 4a constituting the light receiving unit 4. The fourth lens 41 collects the feedback light passed through the second beam splitter 36 to form an image on a second light receiving sensor 4b constituting the light receiving unit 4. The each component of the imaging flow cytometer analyzer 3 operate based on the control by the controller 5. The imaging flow cytometer analyzer 3 may be configured using a technique disclosed in US2015/0192767A1.

The first light receiving sensor 4a takes an x-y plane image of the cell 8 based on the light information of the imaged feedback light. The second light receiving sensor 4b takes an x-z plane image of the cell 8 based on the light information of the imaged feedback light. The first light receiving sensor 4a and the second light receiving sensor 4b each convert the received light information of the plane image into an electric signal and transmit it to the evaluation unit 6 and the database 7. The first light receiving sensor 4a and the second light receiving sensor 4b each operate based on the control by the controller 5.

Next, a description will be given of operations of the cell evaluation system 1 configured as described above. The imaging flow cytometer analyzer 3 physically measures one or more cells flowing in the flow passage 31 based on the above-described configuration. This physical measurement of the cell 8 is performed via any of a visible image, an electromagnetic wave, a fluorescence, a phase, transmission, spectrum, multicolor, scattering, reflection, Coherent Raman, Raman or absorption/scattering/transmission/fluorescence spectrum, a sound, terahertz, or impedance. The following describes an example where a fluorescent image is three-dimensionally measured.

First, the type and the morphology of the cell 8 as the measurement object are not specifically limited insofar as the effects of the present invention is disturbed, and the cell as the measurement object can be selected depending on the object. Accordingly, the cell 8 as the measurement object of the present invention may be a floating cell, or may be an adherent cell. A clear cell includes bacteria (single cell organism). Two or more cells may be the measurement objects, and in such a case, a lump of a plurality of cells (spheroids and the like) may be the measurement object.

Figure 3:
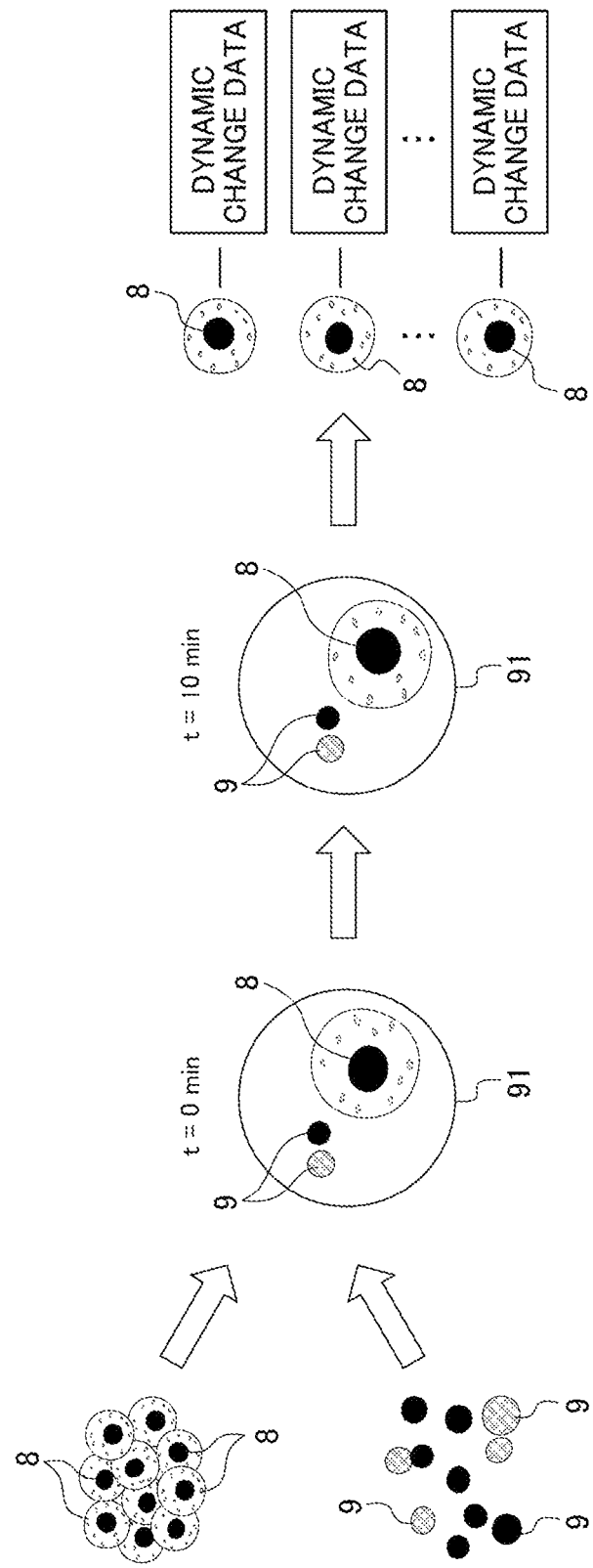
FIG. 3 is a drawing for the explanation of a method for distinguishing a cell as a measurement object.

In distinguishing the cell 8 as the measurement object, as illustrated in FIG. 3, a compartment 91 that includes at least one cell 8 and at least one bead 9 is prepared, and the measurement of both imaging information of the three-dimensional fluorescent image of the cell 8 and imaging information of the bead 9 in each compartment 91 may be repeated over time. The imaging information of the bead 9 in each compartment 91 is used as an indicator to identify the cell 8 in each compartment 91.

The number of the cells 8 as the measurement object is preferably one per compartment 91 from the aspect of the single cell analysis, but not limited to this, the number of the cells 8 per compartment 91 may be plural. When the cell 8 transforms in time series from t=0 (min) to t=10 (min), or the cell 8 exhibits a dynamic behavior, the compartment 91 can be identified by having the bead 9 as the indicator, and eventually, the cell 8 included in this can be identified. Consequently, time-series dynamic change data focused on the one cell 8 can be continuously obtained.

The cell 8 flowing through the flow passage 31 is irradiated with a light in a visible range from the light source 2 via the first objective lens 32, and its feedback light is collected by the first objective lens 32, reflected by the first beam splitter 33, and passes through the first and second lenses 34, 35. Furthermore, a part of this feedback light directly passes through the second beam splitter 36 to form an image on the first light receiving sensor 4a via the third lens 40. The other part of this feedback light is reflected by the second beam splitter 36 and reflected by the mirror 39 to form an image on the second light receiving sensor 4b via the fourth lens 41.

Consequently, the first light receiving sensor 4a takes the x-y plane image of the cell 8, the second light receiving sensor 4b takes the x-z plane image of the cell 8, and the three-dimensional fluorescent image of the cell 8 is formed as the result. Continuously performing this imaging operation while the cell 8 passes through the imaging range of the first objective lens 32 in the flow passage 31 also ensures obtaining the light information of the fluorescent image of three-dimensional entire picture of the cell 8.

The measurement information thus obtained via the first light receiving sensor 4a and the second light receiving sensor 4b is transmitted to the evaluation unit 6 and the database 7.

While the above-described operation example is described for the case where the three-dimensional fluorescent image of the cell 8 is obtained as the physical measurement information, in the case where, provisionally, the two-dimensional plane image is obtained as the physical measurement information, it is only necessary to obtain any of the x-y plane image by the first light receiving sensor 4a or the x-z plane image by the second light receiving sensor 4b.

The evaluation unit 6 analyzes the physical measurement information of the cell 8 transmitted from the first light receiving sensor 4a and the second light receiving sensor 4b to newly evaluate the cell 8. The evaluation unit 6 refers to the information stored in the database 7 in this evaluation process.

Figure 4:
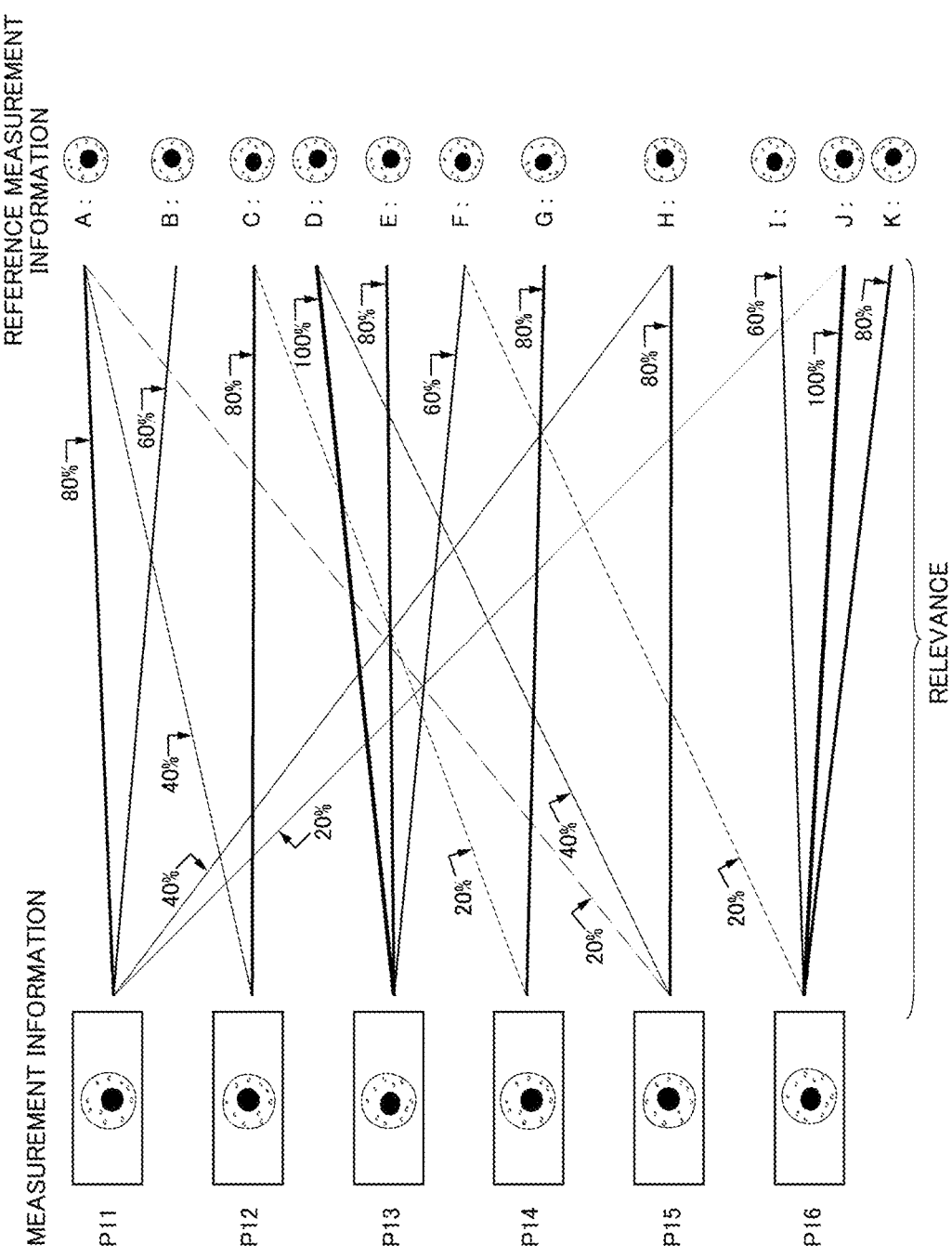
FIG. 4 is a drawing illustrating relevance in three or more levels between measurement information and reference measurement information stored in a database.

The database 7 preliminarily stores, as illustrated in FIG. 4, the relevance in three or more levels between the measurement information and the reference measurement information in advance.

The cell images as the measurement information taken by the above-described imaging flow cytometer analyzer 3 are arranged on the left side via the relevancies, and the reference measurement information is arranged on the right side via the relevancies. The reference measurement information is a list of what is called typical examples of the cell image. The reference measurement information is classified into, for example, images A to K corresponding to the morphological characteristics of the cells.

The relevance indicates that which of the images A to K, which are preliminarily defined as the reference measurement information for each cell morphology, is highly relevant to the cell image, which is newly taken by the imaging flow cytometer analyzer 3 and the like as the measurement information. The cell images as the measurement information are also preliminarily classified into images P11 to P16 as illustrated in FIG. 4. Thus, both the measurement information and the reference measurement information are preliminarily classified for each image, and the classified images P11 to P16 of the measurement information and the images A to K of the reference measurement information are mutually associated via the relevance in three or more levels. In other words, the relevance is an indicator that indicates with which image of the reference measurement information the image of the measurement information is likely to be associated, and the relevance indicates appropriateness in selecting the reference measurement information from the measurement information.

For example, it is indicated that the image P11 of the measurement information has the relevance 80% with the image A of the reference measurement information, the relevance 60% with the image B, the relevance 40% with the image H, and the relevance 20% with the image J. Similarly, it is indicated that the image P13 of the measurement information has the relevance 100% with the image D of the reference measurement information, the relevance 80% with the image E, and the relevance 60% with the image F. Similarly, it is indicated that the image P15 of the measurement information has the relevance 80% with the image H of the reference measurement information, the relevance 40% with the image D, and the relevance 20% with the image A. Incidentally, the thickness of the line connecting the measurement information to the reference measurement information in FIG. 4 indicates the magnitude of the relevance, and when the measurement information and the reference measurement information are not connected with a line, it indicates that the relevance is 0%.

The relevance may be configured as a model that can be updated through what is called a machine learning, and may be configured as a neural network. The relevance may be configured as a network where a deep learning is assumed to be performed.

The evaluation unit 6 thus refers to the relevance stored in the database 7 and determines to which piece of the reference measurement information the measurement information of the cell 8 newly obtained via the light receiving unit 4 (the first light receiving sensor 4*a*, the second light receiving sensor 4*b*) is likely to correspond. When the measurement information of the cell 8 newly obtained via the light receiving unit 4 is similar to the image P14 preliminarily accumulated in the measurement information, it is determined to be most likely to correspond to the image G of the reference measurement information having the highest relevance with the image P14, and it is determined to be next likely to correspond to the image C. When the measurement information of the cell 8 newly obtained via the light receiving unit 4 is similar to the image P16 preliminarily accumulated in the measurement information, it is determined to be most likely to correspond to the image J of the reference measurement information having the highest relevance with the image P16, and it is determined to be next likely to correspond to the image K.

The evaluation unit 6 performs the operation of referring to the relevancies based on the measurement information of the cell 8 newly obtained via the light receiving unit 4 and selecting the image of the reference measurement information. At this time, the evaluation unit 6 may select the image of the reference measurement information having the highest relevance with the measurement information of the cell 8 newly obtained via the light receiving unit 4. This is because, as described above, the higher the relevance is, the higher the appropriateness of the selection becomes. However, the evaluation unit 6 is not limited to the case where the image of the reference measurement information having the highest relevance is selected, but may be configured to purposely select the one having the medium relevance or the one having the low relevance. In addition, the reference measurement information having the relevance of 0% where the measurement information and the reference measurement information are not connected with a line may be naturally selected. Incidentally, the evaluation unit 6 is not limited to the case where one piece of the reference measurement information is selected, but may be configured to refer to the relevance and purposely select a plurality of pieces of the reference measurement information.

Figure 5:
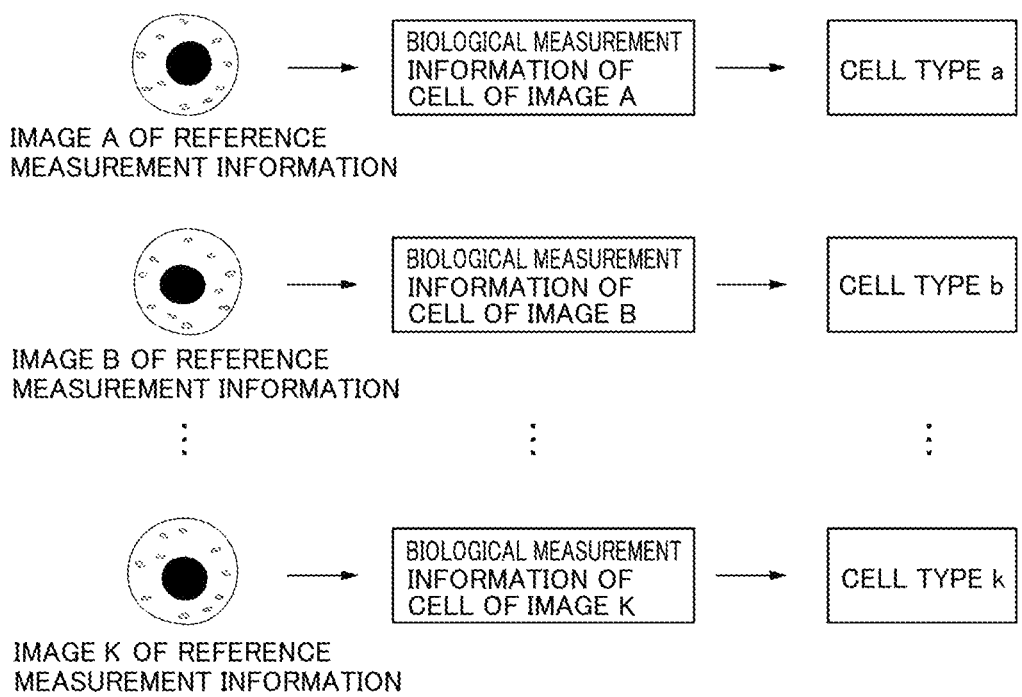
FIG. 5 is a drawing illustrating a process of identifying a cell type from selected reference measurement information.

Next, the evaluation unit 6 identifies the cell type from the selected reference measurement information. FIG. 5 illustrates a process of identifying the cell type from the selected reference measurement information. Each piece of the reference measurement information is associated with biological measurement information. The reference measurement information and the biological measurement information are ordinarily associated in one-to-one, but not limited to this, and may be mutually associated one-to-multiple, multiple-to-one, or multiple-to-multiple.

The biological measurement information is information measured via, for example, a time series change trend of transcriptome, genome, epigenome, protein, metabolite, sugar, lipid, and a cell for identifying the cell type. The biological measurement information is the information previously obtained via the transcriptome, the genome, and the like for each cell of the images A to K constituting the reference measurement information. Obtaining the biological measurement information for each cell of the images A to K ensures identifying the accurate type of the cell for each cell of the images A to K. The respective pieces of the biological measurement information correspond to the cell types identified from them ordinarily in 1-to-1. In this example of FIG. 5, when the result of obtaining the biological measurement information of the cell of the image A of the reference measurement information is "genome XXX," a cell type a can be identified from the "genome XXX." When the result of obtaining the biological measurement information of the cell of the image B of the reference measurement information is "lipid time series change trend YYY," a cell type b can be identified from the "lipid time series change trend YYY." When the result of obtaining the biological measurement information of the cell of the image K of the reference measurement information is "transcriptome ZZZ," a cell type k can be identified from the "transcriptome ZZZ." Further, the biological measurement information includes optical imaging measurement information for obtaining finer or different optical information. That is, the biological measurement information is a concept including imaging (morphology) analysis result in addition to the cell type and the like.

The database 7 stores the biological measurement information corresponding to each piece of the reference measurement information as illustrated in FIG. 5, and further stores the cell types identified from the biological measurement information. Therefore, the evaluation unit 6 refers to the database 7 to determine the biological measurement information associated with the selected reference measurement information, and determines the cell type identified from the determined biological measurement information.

That is, when the reference measurement information can be selected as illustrated in FIG. 6, the evaluation unit 6 can immediately determine the cell type via the biological measurement information. The evaluation unit 6 indicates the determined cell type via a display unit (not illustrated) including a display and the like. Accordingly, a user can immediately understand the cell type of the newly obtained cell 8 by visually perceiving the display unit (not illustrated).

That is, the cell evaluation system 1 to which the present invention is applied can select the reference measurement information from the measurement information of the cells newly obtained via the imaging flow cytometer analyzer 3 by referring to the above-described relevance, and further determine the cell type from the reference measurement information via the biological measurement information. Moreover, the cell evaluation system 1 to which the present invention is applied can automatically perform these evaluation operations without human intervention. This ensures the high-speed and accurate classification and evaluation of the cell information based on the physical measurement information, not based on the subjective determination by an observer but based on the biologically straight correctinformation. Since the cell type of each of the individual cells identified by the imaging flow cytometer analyzer 3 with an imaging flow cytometry technology can be automatically identified, the enormous volume of information generated by this technology can be effectively utilized.

In the cell evaluation system 1 to which the present invention is applied, the reference measurement information is searched via the relevance set in three or more levels. While the relevance can be described with numerical values of, for example, 0 to 100%, the relevance is not limited to this, and may be configured in any levels insofar as the relevance can be described with the numerical values in three or more levels.

The search based on such a relevance indicated by the numerical value in three or more levels ensures the search to display in descending order of the relevance under the condition where a plurality of pieces of the reference measurement information are selected. When the relevance can be thus displayed to the user in the descending order, the reference measurement information with higher probability can be preferentially picked up, and eventually, the cell type identified from it can be displayed. Meanwhile, even for the reference measurement information having the low relevance, the cell type identified from it can be displayed in the sense of second opinion, and this can provide usefulness in the case where the cell type displayed in the first opinion is incomprehensible or similar case.

In addition, according to the present invention, even the reference measurement information having an extremely low relevance, for example, 1% can be determined without missing. This can bring to the user's attention that even the reference measurement information having an extremely low relevance is connected as a slight sign and may be useful as the reference measurement information once every tens of times, or once every hundreds of times.

Furthermore, according to the present invention, since the search is performed based on the relevance in three or more levels, an advantage is provided in that a search policy can be determined by the way of setting a threshold. While decreasing the threshold ensures picking up even the one having the relevance of 1% as described above without missing, many cell types having low probability of correct answer are possibly picked up based on the reference measurement information. Meanwhile, while increasing the threshold ensures narrowing down to only the cell types identified by the reference measurement information having the high possibility of correct answer, the cell type identified by the reference measurement information indicating an appropriate answer once every tens of times, or once every hundreds of times is possibly missed. While to which emphasis is placed can be determined based on the way of thinking on the user side or the system side, thus the degree of freedom in selecting the point to be emphasized can be more flexible.

According to the present invention, for the measurement information in FIG. 4, while the description is given with the exemplary case where the relevance of the reference measurement information is previously set for each piece of the measurement information P11 to P16, this should not be construed in a limiting sense. Combinations of the measurement information and the relevance in three or more levels with the reference measurement information are stored in advance, and the evaluation may be performed based on the newly physically measured two or more pieces of measurement information.

In this case, assume that, for example, the relevance of the reference measurement information D is defined as 60%, and the relevance of the reference measurement information E is defined as 40% for the combination of the measurement information P11 and, P12. Alternatively, it is defined such that the relevance of the reference measurement information H is 20%, the relevance of the reference measurement information I is 50%, the relevance of the reference measurement information J is 70%, and the like for the combination of three pieces of the measurement information P13, P14, and P15.

Provisionally, when the newly obtained two or more pieces of the measurement information are the measurement information P11 and the measurement information P12, with reference to these relevancies, the fact that the relevance of the reference measurement information D is 60%, the relevance of the reference measurement information E is 40%, and the like can be determined. The reference measurement information is similarly selected with reference to these relevancies. Similarly, provisionally, when the newly obtained two or more pieces of the measurement information are the measurement information P13, the measurement information P14, and the measurement information P15, with reference to these relevancies, the fact that the relevance of the reference measurement information H is 20%, the relevance of the reference measurement information I is 50%, and the relevance of the reference measurement information J is 70% can be determined. The reference measurement information is similarly selected with reference to these relevancies.

This example where the combination of the measurement information and the relevance in three or more levels with the reference measurement information are referred may be applied to what is called a multiple-instance learning and the like where a comparative verification is performed especially between sets of captured images of the cells.

In this case, cell images relevant to a disease are each stored as the reference measurement information in advance. Next, a plurality of cell images may be taken as the measurement information for each of a plurality of cells of a patient A to determine whether the disease corresponds to a disease matching up with the reference measurement information or not by referring to the relevance.

In the present invention, the above-described relevance may be updated. That is, the measurement information and the reference measurement information as illustrated in FIG. 4 are updated as needed. This update may be performed by, for example, reflecting information provided via a public communications network including Internet. The update may be artificially or automatically performed on the system side or the user side based on contents of research data and an article by an expert, an academic conference presentation, a newspaper article, a book, and the like. In these update processes, an artificial intelligence may be used.

The update of the relevance increases or decreases the relevance every time when information on the relationship between the measurement information and the reference measurement information is obtained. For example, when it is newly confirmed that the image of one piece of the measurement information corresponds to the image of one piece of the reference measurement information by the article, the academic conference presentation, or the research data and the like based on any experimental validation, the relevance between that image of the measurement information and the image of the reference measurement information is increased. When it is newly confirmed that the image of one piece of the measurement information does not correspond to the image of one piece of the reference measurement information by the article, the academic conference presentation, or the research data and the like based on any experimental validation, the relevance between that image of the measurement information and the image of the reference measurement information is decreased.

The relevance can be freely corresponded when the relevance is desired to be increased or decreased because the relevance is configured in three or more levels as described above. The update of the relevance itself may be performed through the above-described machine learning and deep learning.

Furthermore, in the case where an image of the measurement information that has not been obtained so far is newly taken, when it is experimentally confirmed that this actually corresponds to one piece of the reference measurement information, the relevance may be newly set between them. Then, every time when the report that this new measurement information corresponds to this reference measurement information is made, this newly set relevance may be gradually increased.

In the embodiment described above, the case where the reference measurement information each associated with the biological measurement information for identifying the cell type is selected is described as an example. The present invention is not limited to this example of identifying the cell type, but may be applied to the case where the function and the characteristics of the cell are evaluated. In this case, not the cell type but the function of the cell and the characteristics of the cell are identified by the biological measurement information illustrated in FIG. 5. Also in this case, similarly, the correspondence relation between each piece of the biological measurement information, and each function of the cell and each characteristic of the cell is previously obtained and stored in the database 7. As a result, as illustrated in FIG. 6, when the image of the reference measurement information is selected, each function of the cell and each characteristic of the cell substituted for the cell type are immediately determined via the biological measurement information.

While the embodiment described above is described with the exemplary case where the measurement information is obtained via the two-dimensional or three-dimensional fluorescent image, the same applies to another case where the cell 8 is physically measured with any of an electromagnetic wave, a bright field, a dark field, a fluorescence, a phase, transmission, spectrum, multicolor, scattering, reflection, Coherent Raman, Raman or absorption/scattering/transmission/fluorescence spectrum, a sound, terahertz, or impedance to obtain the measurement information. In this case, typical examples of the reference measurement information are also prepared in advance in accordance with the physical measurement means, and mutual association is previously performed with the relevance.

For example, when the physical measurement means is a fluorescence spectrum analysis, both the measurement information and the reference measurement information are fluorescence spectra. For the reference measurement information, a peak position of each wavelength, a change trend, and the like are previously classified. The reference measurement information is selected by referring to the relevance for the classified fluorescence spectrum patterns as the reference measurement information based on the measurement information including the fluorescence spectra newly obtained from the cell 8.

The physical measurement means may be based on any method such as an observation method using a microscope including a compartment observation method in a microwell using a microscope, and an imaging cytometry method, in addition to the imaging flow cytometry method. The present invention may be applied to a case where cells not in a liquid are measured, in addition to the case where the cells flowing down in the liquid are physically measured. The microscope to be used may be an optical microscope (including the bright field, a phase difference, a fluorescence, a confocal laser, a Raman, and the like), an electron microscope (a transmission type, scanning type), or the like.

Figure 7:
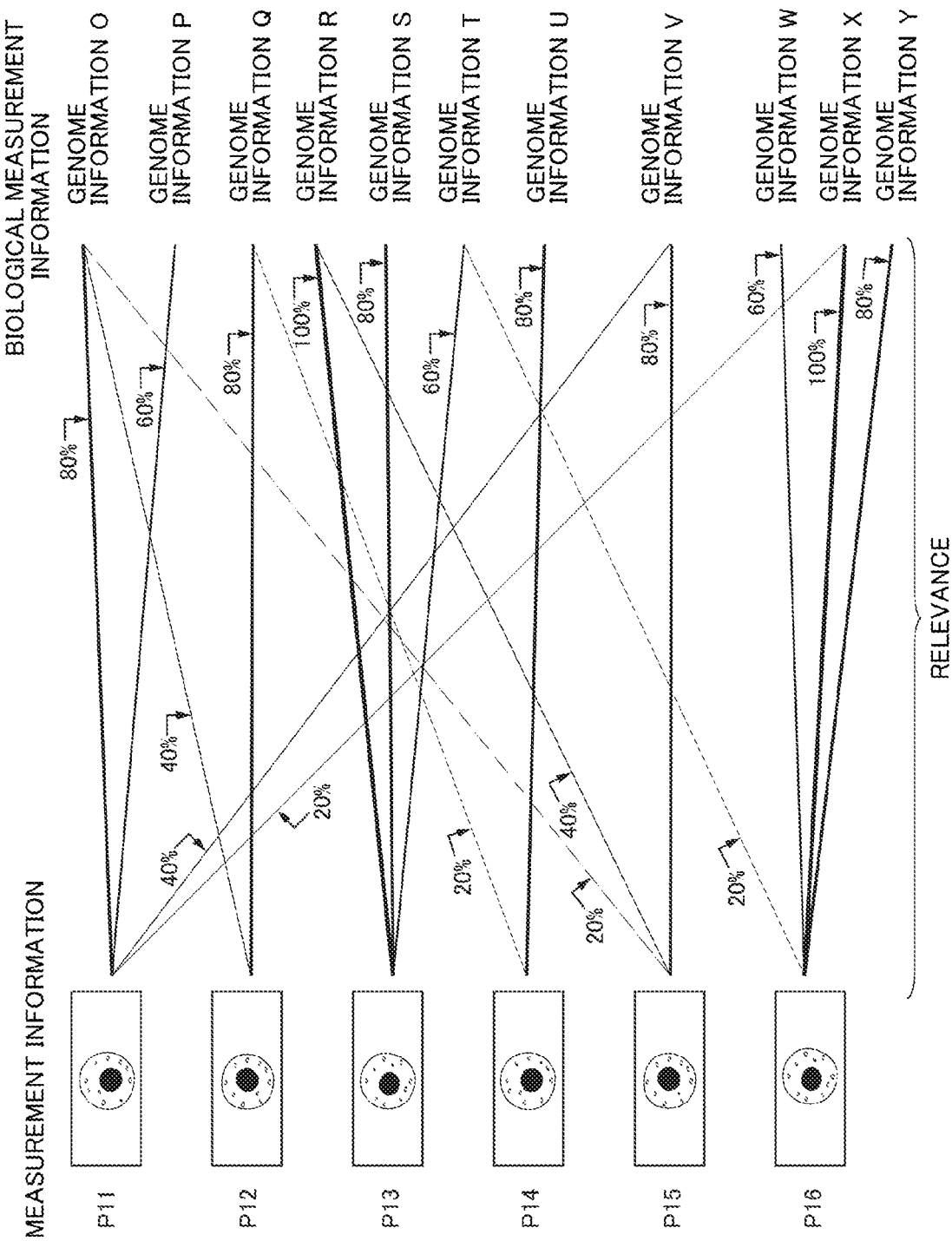
FIG. 7 is a drawing illustrating the relevance in three or more levels between the measurement information and the biological measurement information.

In the present invention, as illustrated in FIG. 7, the relevance in three or more levels between the measurement information and the biological measurement information may be previously stored.

The cell images as the measurement information taken by the above-described imaging flow cytometer analyzer 3 are arranged on the left side via the relevancies, and the biological measurement information is arranged on the right side via the relevancies. The biological measurement information is, for example, a list of various kinds of genome information and the like for identifying each of the cell types (the function, the characteristic, and the like of the cell). The biological measurement information is previously classified corresponding to the genome information and the like, and as illustrated in FIG. 7, classified into the genome information O to the genome information Y, and the like.

The relevance indicates that which of the genome information O to the genome information Y and the like, which are previously classified as the biological measurement information, is highly relevant to the cell image, which is newly taken by the imaging flow cytometer analyzer 3 and the like as the measurement information, and mutually associated via the relevance in three or more levels. In other words, the relevance is an indicator that indicates with which piece of the biological measurement information the image of the measurement information is likely to be associated, and the relevance indicates appropriateness in selecting the biological measurement information from the measurement information.

For example, it is indicated that the image P11 of the measurement information has the relevance 80% with the genome information O of the biological measurement information, the relevance 60% with the genome information P, the relevance 40% with the genome information V, and the relevance 20% with the genome information X. Similarly, it is indicated that the image P13 of the measurement information has the relevance 100% with the genome information R of the biological measurement information, the relevance 80% with the genome information S, and the relevance 60% with the genome information T. Incidentally, the thickness of the line connecting the measurement information to the biological measurement information in FIG. 7 indicates the magnitude of the relevance, and when the measurement information and the biological measurement information are not connected with a line, it indicates that the relevance is 0%.

This relevance may be similarly configured as a model that can be updated through what is called a machine learning, and may be configured as a neural network. This relevance may be configured as a network where a deep learning is assumed to be performed.

The evaluation unit 6 thus refers to the relevance stored in the database 7 and determines to which piece of the biological measurement information the measurement information of the cell 8 newly obtained via the light receiving unit 4 (the first light receiving sensor 4a, the second light receiving sensor 4b) is likely to correspond. When the measurement information of the cell 8 newly obtained via the light receiving unit 4 is similar to the image P14 preliminarily accumulated in the measurement information, it is determined to be most likely to correspond to the genome information U of the biological measurement information having the highest relevance with the image P14, and it is determined to be next likely to correspond to the genome information Q. When the measurement information of the cell 8 newly obtained via the light receiving unit 4 is similar to the image P16 preliminarily accumulated in the measurement information, it is determined to be most likely to correspond to the genome information X of the biological measurement information having the highest relevance with the image P16, and it is determined to be next likely to correspond to the genome information Y.

The evaluation unit 6 performs the operation of referring to the relevancies to select the biological measurement information based on the measurement information of the cell 8 newly obtained via the light receiving unit 4. At this time, the evaluation unit 6 may select the biological measurement information having the highest relevance with the measurement information of the cell 8 newly obtained via the light receiving unit 4. This is because, as described above, the higher the relevance is, the higher the appropriateness of the selection becomes. However, the evaluation unit 6 is not limited to the case where the image of the biological measurement information having the highest relevance, but may be configured to purposely select the one having the medium relevance or the one having the low relevance. In addition, the biological measurement information having the relevance of 0% where the measurement information and the biological measurement information are not connected with a line may be naturally selected. Incidentally, the evaluation unit 6 is not limited to the case where one piece of the biological measurement information is selected, but may be configured to refer to the relevance and purposely select a plurality of pieces of the biological measurement information.

Next, the evaluation unit 6 identifies the cell type from the selected biological measurement information. Since the biological measurement information is originally associated with the cell type, when the biological measurement information can be selected, the cell type can be immediately identified. Previously associating the evaluation of the function and the characteristic of the cell other than the cell type with the biological measurement information ensures the cell evaluation other than the cell type.

The relevance between the measurement information and the biological measurement information as illustrated in FIG. 7 may be updated. This update may be performed by, for example, reflecting information provided via a public communications network including Internet. The update may be artificially or automatically performed on the system side or the user side based on contents of research data and an article by an expert, an academic conference presentation, a newspaper article, a book, and the like. In these update processes, an artificial intelligence may be used.

The update of the relevance increases or decreases the relevance every time when the information on the relationship between the measurement information and the biological measurement information is obtained. For example, when it is newly confirmed that the image of one piece of the measurement information corresponds to the genome information of one piece of the biological measurement information by the article, the academic conference presentation, or the research data and the like based on any experimental validation, the relevance between that image of the measurement information and the genome information of the biological measurement information is increased. When it is newly confirmed that the image of one piece of the measurement information does not correspond to the genome information of one piece of the biological measurement information by the article, the academic conference presentation, or the research data and the like based on any experimental validation, the relevance between that image of the measurement information and the genome information of the biological measurement information is decreased.

Second Embodiment

The following describes a cell evaluation system 1' according to the second embodiment in detail with reference to the drawings. In this second embodiment, identical reference numerals are attached to the components and the members identical to those of the above-described first embodiment, and the descriptions will be omitted below.

Figure 8:
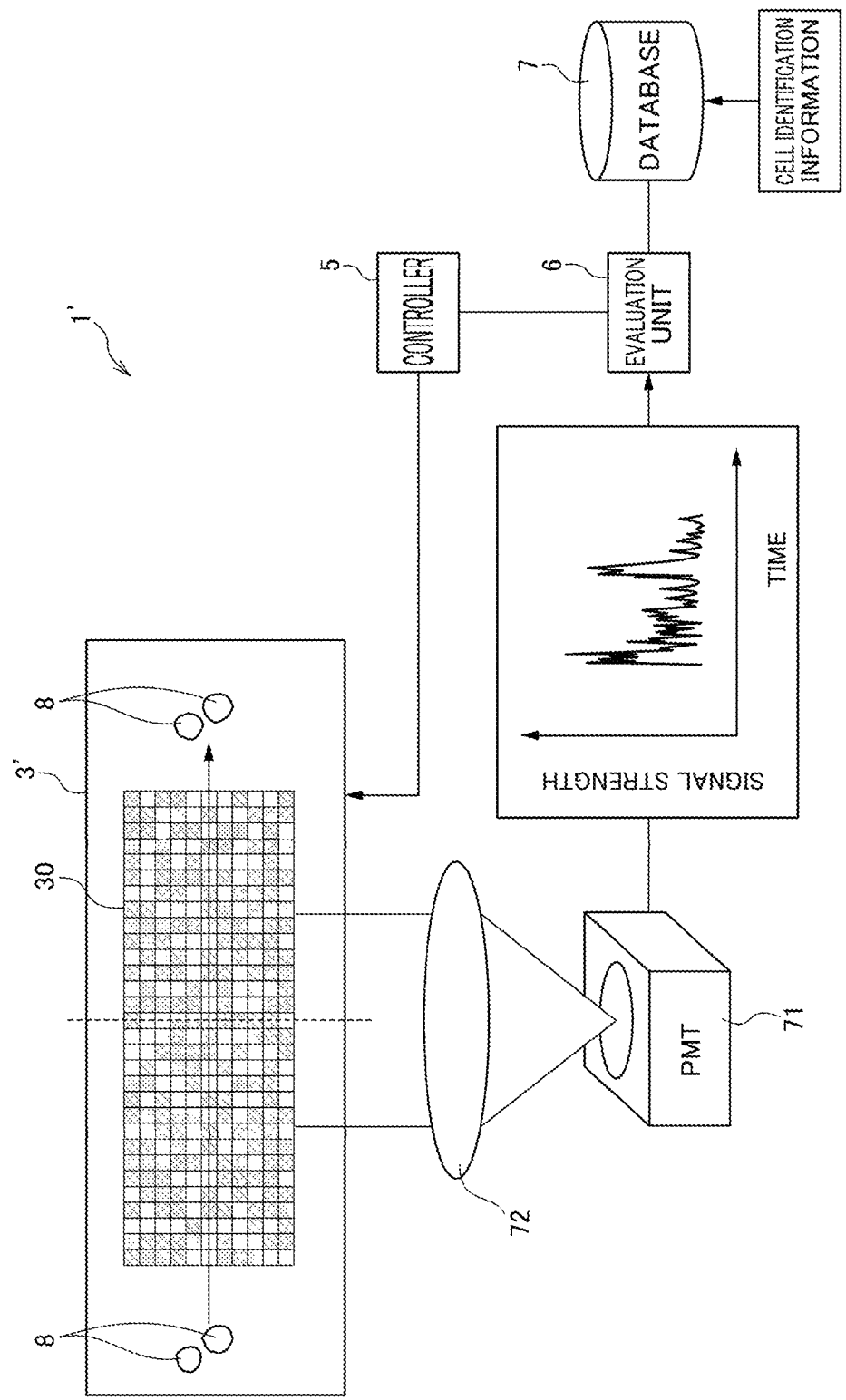
FIG. 8 is a block configuration diagram of a cell evaluation system in the second embodiment.

FIG. 8 illustrates a configuration of the cell evaluation system 1' to which the present invention is applied. The cell evaluation system 1' includes an imaging flow cytometer analyzer 3', a lens 72 connected to the imaging flow cytometer analyzer 3', and a PMT (one-pixel element) 71 to which the light is introduced from the lens 72. The cell evaluation system 1' includes the evaluation unit 6 that evaluates data detected by the PMT 71, and the controller 5 and the database 7 each connected to the evaluation unit 6.

This known static random structure illumination unit 30 has a light structure that emits an excitation light via a specific shading pattern, performing what is called a structured lighting. This known static random structure illumination unit 30 is designed based on a design method by a compressed sensing or any design method other than this. The excitation light or the illuminating light structured by the light structure can be emitted to form a light pattern on a sample surface. A cell group including the cell 8 as the measurement object flows down through a flow passage of the known static random structure illumination unit 30. As a result, the cell group as the measurement object flowing down in the flow passage is irradiated with the excitation light. The individual cell 8 passes through an optical element such as a diffraction element and interacts with the excitation light in time series. Mapping optical space information (morphological information) of this cell 8 in time series ensures the physical measurement. What is called a ghost cytometry method may be applied to the imaging flow cytometer analyzer 3'. While the cell image may be reconstructed based on an obtained waveform signal, the reconstruction of the cell image is not especially required in the second embodiment.

That is, the excitation light excites different parts of the cell 8 in time series to cause the interaction, and the space information of the cell 8 is compressed and converted into time information. The movement of the cell 8 flowing in the imaging flow cytometer analyzer 3' and the emission of the excitation light (illuminating light) from the known static random structure illumination unit 30 progress to cause a change on a part where the excitation light (illuminating light) overlaps the cell, and a temporal change of total amount of overlapping is measured. That is, a time series waveform as illustrated in FIG. 8 having a horizontal axis as a time axis and a vertical axis as a signal strength axis can be detected.

The time series waveform is detected by the PMT 71 that is the high speed and highly sensitive one-pixel element. The lens 72 guides the light from the imaging flow cytometer analyzer 3' to the PMT 71 and collects the light, thus measuring the signal for one pixel.

The evaluation unit 6 searches cell identification information of the cell flowing in the imaging flow cytometer analyzer 3' based on thus obtained time series waveform. The cell identification information here is a concept including any information for identifying the cell flowing in the imaging flow cytometer analyzer 3', and information for specifying, for example, a cell phenotype, cell characteristics, a cell type, intracellular molecular localization, an intracellular structure, cell morphology, cell maturity, and those important cell characterizations. In the following example, a description will be given with an exemplary case where the cell type of the cell flowing in the imaging flow cytometer analyzer 3' is searched as the cell identification information.

On searching the cell identification information, the evaluation unit 6 establishes and stores a learned model in the database 7 in advance. The exemplary learned model is illustrated in FIG. 9.

Figure 9:
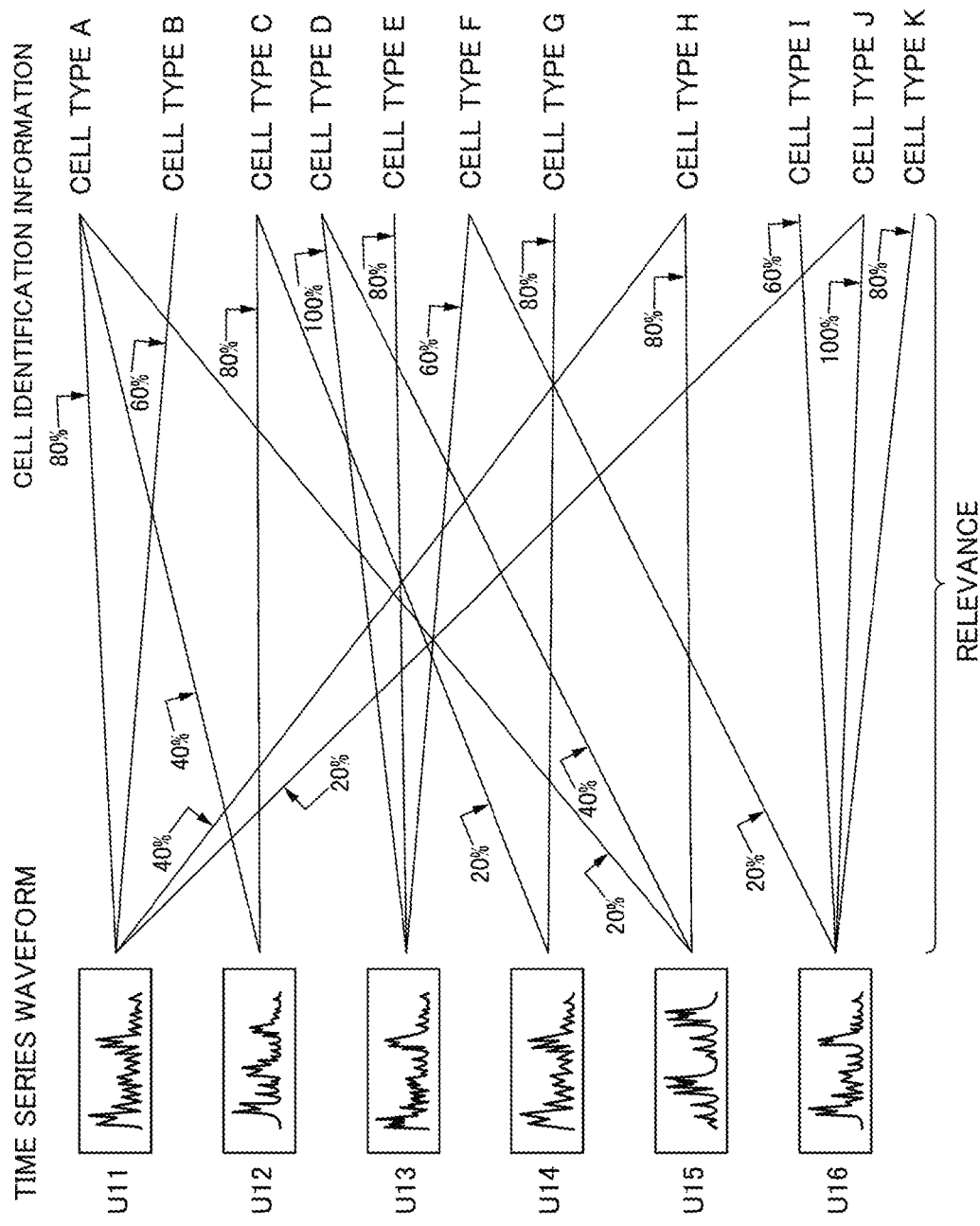
FIG. 9 is a drawing illustrating an example of a learned model in the second embodiment.

As illustrated in FIG. 9, the time series waveforms are arranged on the left side via the relevancies, and the cell identification information (cell type) is arranged on the right side via the relevancies. While the relevance is similar to that in the above-described example of FIG. 4, in this example, the relevance indicates with which piece of the cell identification information the time series waveform is highly relevant.

For example, it is indicated that the time series waveform U11 has the relevance 80% with the cell type A of the cell identification information, the relevance 60% with the cell type B, the relevance 40% with the cell type H, and the relevance 20% with the cell type J. Similarly, it is indicated that the time series waveform U13 has the relevance 100% with the cell type D of the cell identification information, the relevance 80% with the cell type E, and the relevance 60% with the cell type F. Similarly, it is indicated that the time series waveform U15 has the relevance 80% with the cell type H of the cell identification information, the relevance 40% with the cell type D, and the relevance 20% with the cell type A. Incidentally, when the time series waveform and the cell identification information are not connected with a line, it indicates that the relevance is 0%.

The relevance may be configured as a model that can be updated through what is called a machine learning, and may be configured as a neural network. The relevance may be configured as a network where a deep learning is assumed to be performed.

The evaluation unit 6 thus refers to the relevance stored in the database 7 and determines to which piece of the cell identification information the time series waveform of the cell 8 newly obtained via the PMT 71 is likely to correspond. When the newly obtained time series waveform of the cell 8 is similar to the time series waveform U14, it is determined to be most likely to correspond to the cell type G of the cell identification information having the highest relevance with the U14, and it is determined to be next likely to correspond to the cell type C. When the newly obtained time series waveform of the cell 8 is similar to U16, it is determined to be most likely to correspond to the cell type J of the cell identification information having the highest relevance with the U16, and it is determined to be next likely to correspond to the cell type K.

Incidentally, also when it is determined to which time series waveform U of the learned model stored in the database 7 the newly obtained time series waveform is similar, the artificial intelligence methods, such as the deep learning and the machine learning may be used.

The evaluation unit 6 performs the operation of referring to the relevancies based on newly obtained time series information of the cell 8 and selecting any one or more pieces of the cell identification information. At this time, the evaluation unit 6 may select the cell identification information having the highest relevance with the time series information of the cell 8 newly obtained via the controller 5. This is because, as described above, the higher the relevance is, the higher the appropriateness of the selection becomes. However, the evaluation unit 6 is not limited to the case where the image of the cell identification information having the highest relevance is selected, but may be configured to purposely select the one having the medium relevance or the one having the low relevance. In addition, the cell identification information having the relevance of 0% where the time series information and the cell identification information are not connected with a line may be naturally selected. Incidentally, the evaluation unit 6 is not limited to the case where one piece of the cell identification information is selected, but may be configured to refer to the relevance and purposely select a plurality of pieces of the cell identification information.

Incidentally, the relevance may be an alternative to a neuron of the neural network. In this case, the learned model where one or more pieces of the cell identification information are associated with the combination of a plurality of the time series waveforms via the relevancies is established in advance. Then, in the actual determination, the one or more pieces of the cell identification information may be selected based on the above-described method.

Figure 10:
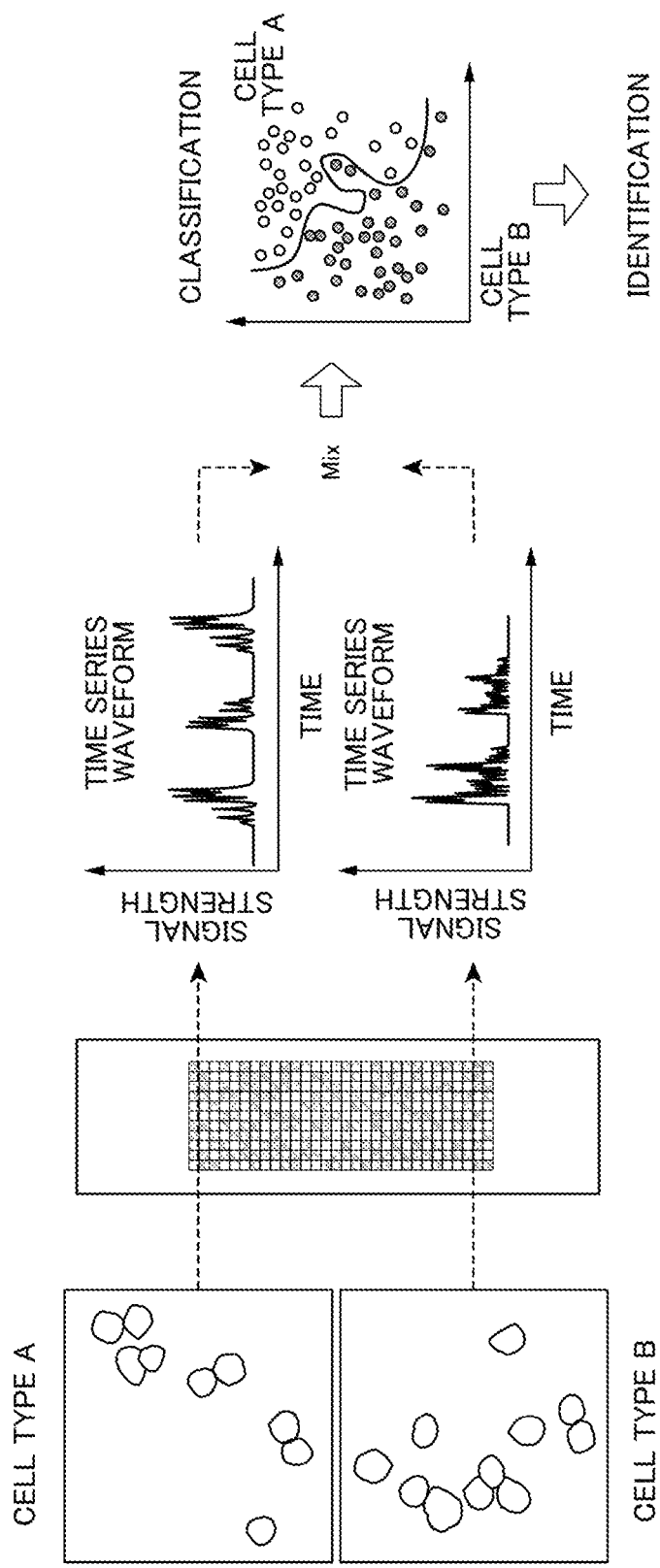
FIG. 10 is a drawing illustrating an example of learning by tagging a time series waveform for each piece of cell identification information.

FIG. 10 illustrates an example of learning by tagging a time series waveform for each piece of the cell identification information. That is, the time series waveform is learned for each of the cell types A and B. The learned model where the time series waveform is learned for each piece of the cell identification information via the relevance in three or more levels is stored in advance. The exemplary learned model is the above-described network illustrated in FIG. 9. Next, to which piece of the cell identification information (cell type A, cell type B) the time series waveform of the cell 8 newly obtained via the PMT 71 corresponds is determined as described above.

Figure 11:
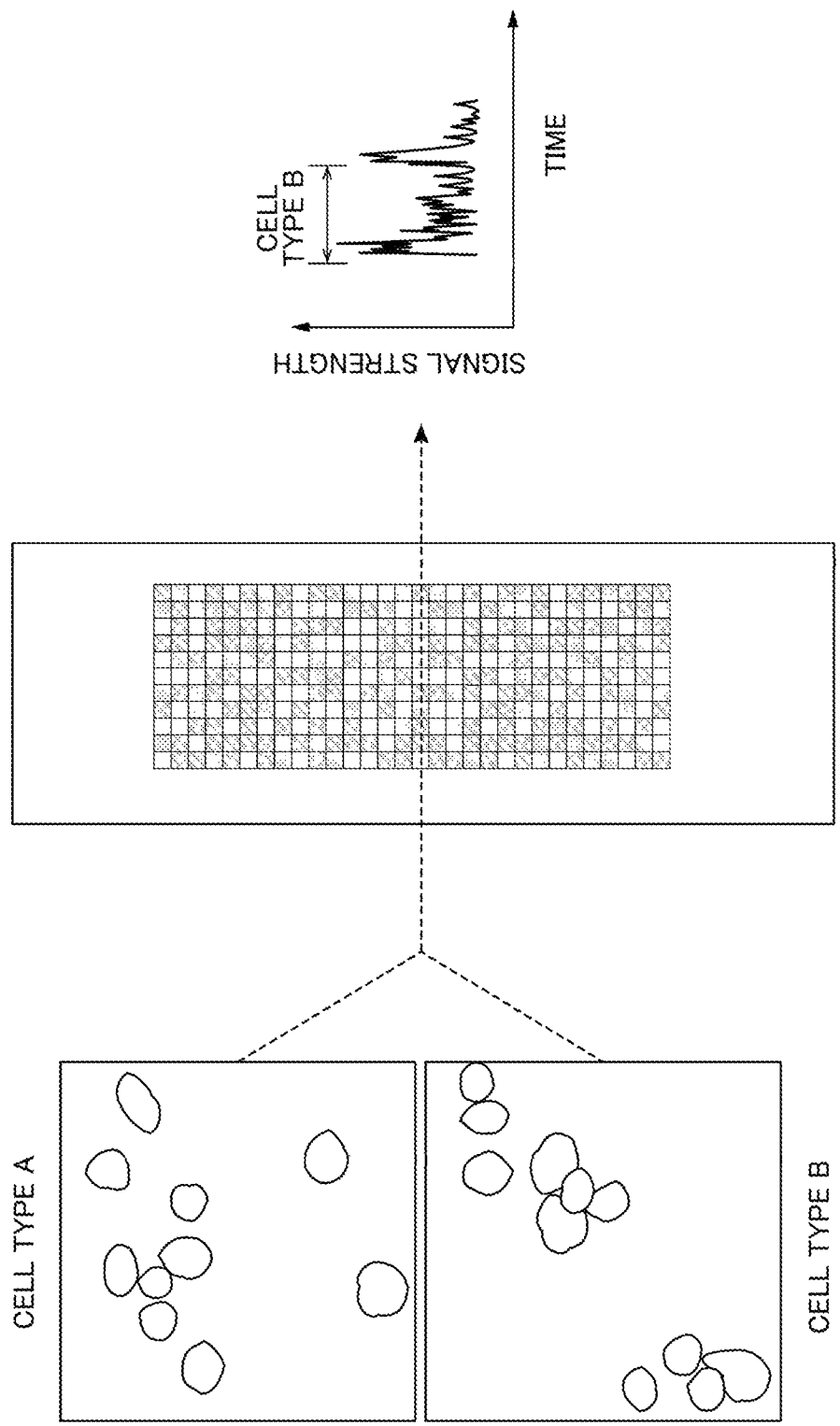
FIG. 11 is a drawing illustrating an example of learning with the relevance in three or more levels between a time series waveform of a mixture where a plurality of pieces of the cell identification information are mixed and each piece of the cell identification information.

FIG. 11 illustrates an example of learning via the relevance in three or more levels between the time series waveforms of a mixture where a plurality of pieces of the cell identification information are mixed and each piece of the cell identification information. That is, in the establishment stage of the learned model, the time series waveforms of the mixture where the cell type A and the cell type B are mixed are obtained in advance. The time series waveforms obtained thereby include both of a sign corresponding to the cell type A and a sign corresponding to the cell type B. The time series waveforms are learned as the learned model in advance, and the cell group with which the cell 8 as the measurement object is combined is newly obtained via the PMT 71. The sign corresponding to the cell type A and the sign corresponding to the cell type B in time series waveforms obtained from there are each compared with the learned model, and determined to which the signs correspond.

The learned model in this case includes the time series waveforms arranged on the left side of the relevance illustrated in FIG. 9, and the time series waveforms are any one of the sign corresponding to the cell type A and the sign corresponding to the cell type B, or the combination of both signs. The respective pieces of the cell identification information are tagged to the time series waveforms via the relevancies, thus constituting the learned model. As a result of newly obtaining the time series waveforms via the PMT 71 from the cell group with which the cell 8 as the measurement object is combined, and comparing with the learned model, when it is determined that the sign of the cell type B is included as illustrated in FIG. 11, it can be determined that the obtained cell group includes the cell type B.

Figure 12:
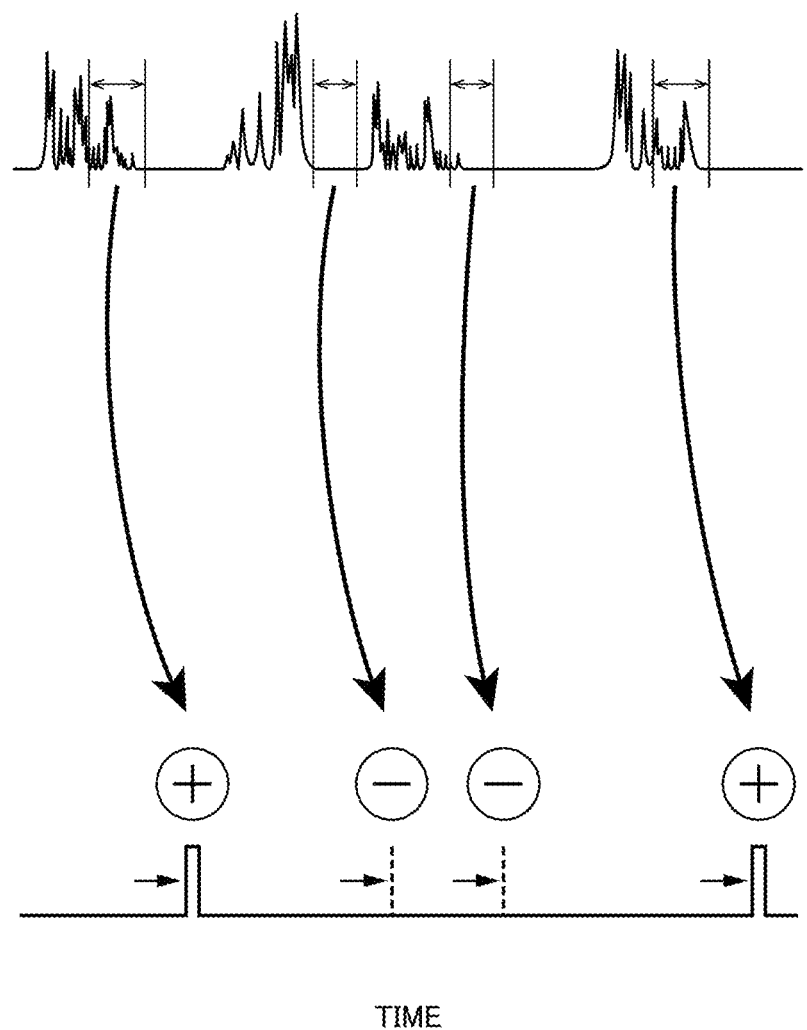
FIG. 12 is a drawing illustrating an example of establishing the learned model based on a positive time series waveform and a negative time series waveform in identifying the cell identification information to be detected.

FIG. 12 illustrates an example of establishing a learned model where a positive time series waveform and a negative time series waveform in identifying the cell identification information to be detected are previously learned via the relevance in three or more levels. Similarly, to the example of FIG. 11, the positive time series waveform and the negative time series waveform in detecting specific cell identification information (for example, the cell type B) from the time series waveforms of the mixture where a plurality of pieces of the cell identification information are mixed are learned in advance. The positive time series waveform here is a sign of the waveform having a high probability of corresponding to the specific cell identification information (for example, the cell type B). Meanwhile, the negative time series waveform is a sign of the waveform having a low probability of corresponding to the specific cell identification information (for example, the cell type B). In this case, the time series waveforms are arranged on the left side of the relevancies illustrated in FIG. 9, and positive or negative are arranged on the right side of the relevancies and each associated via the relevancies.

Then, as a result of newly obtaining the time series waveforms via the PMT 71 from the cell group with which the cell 8 as the measurement object is combined, and comparing with the learned model, the probability of corresponding to the specific cell identification information (for example, the cell type B) is increased when the sign of the positive time series waveform appears, while the probability of corresponding to the specific cell identification information (for example, the cell type B) is decreased when the sign of the negative time series waveform appears. That is, the closer to the positive time series waveform, the more negative determination is made in determining the cell identification information to be detected, and the closer to the negative time series waveform, the more positive determination is made in determining the cell identification information to be detected. Finally, the positive sign and the negative sign corresponding to this specific cell identification information are comprehensively determined, and the probability of corresponding to the specific cell identification information is determined.

In this case, the learned model where only the negative time series waveform in identifying the cell identification information to be detected is previously learned via the relevance in three or more levels may be stored. Then, when the time series waveforms are newly obtained via the PMT 71 from the cell group with which the cell 8 as the measurement object is combined, whether to correspond to the negative time series waveform or not is determined with reference to the learned model. As a result, the one not corresponding to the negative time series waveform may be identified as the cell identification information to be detected.

In FIG. 12, "+" is the positive sign and "−" is the negative sign, and an example where the control by the controller 5 is changed every time when each of the signs is detected is illustrated. In the case of a configuration where the imaging flow cytometer analyzer 3' has a branched tip and the cells can be classified through the control by the controller 5, the specific cell 8 may be guided to a branched specific flow passage only when the positive sign appears. In this case, the controller 5 may naturally guide the specific cell 8 with every physical means via an electric field, a magnetic field, and the like.

Figure 13:
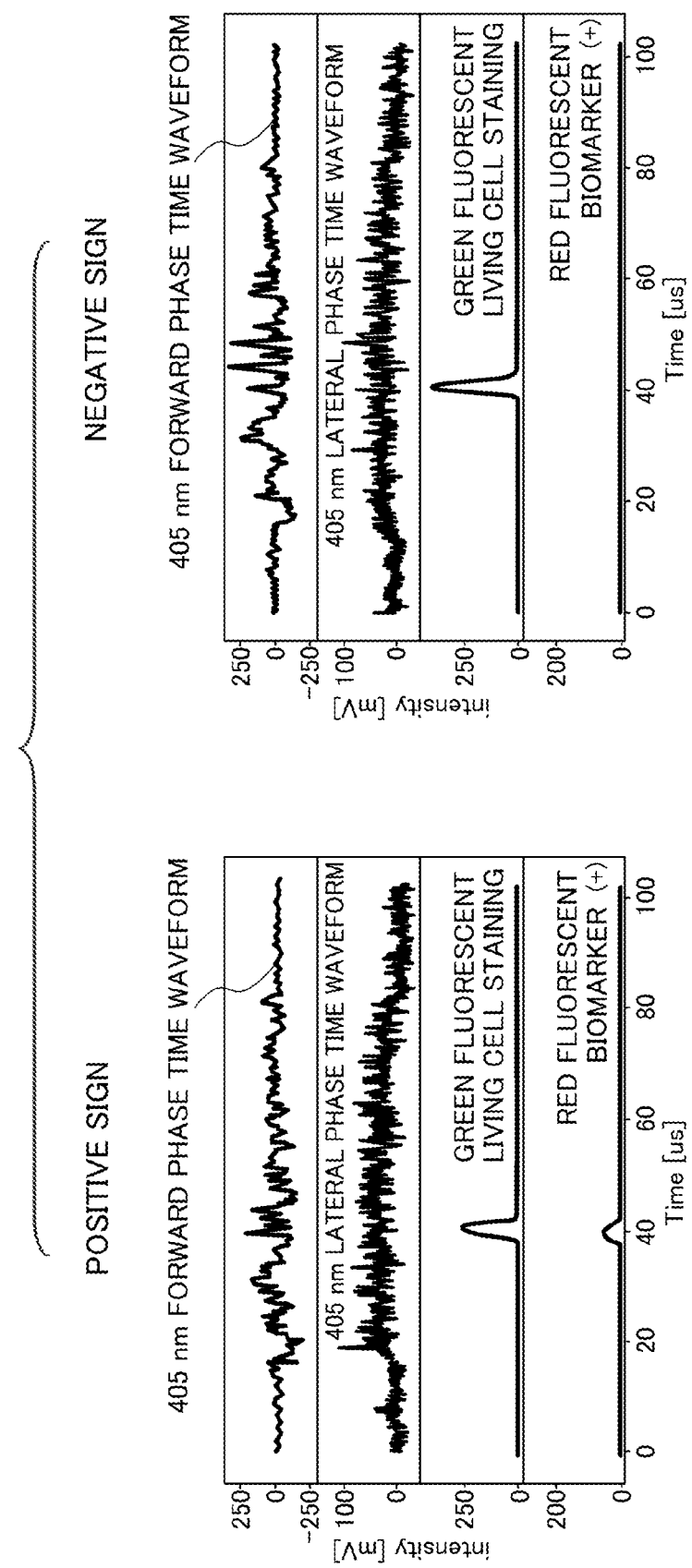
FIG. 13 is a drawing illustrating an example of establishing the learned model by obtaining a positive sign and a negative sign with the cell identification information.

FIG. 13 illustrates an example of establishing the learned model by obtaining the positive sign and the negative sign with the cell identification information. With the time series waveform exhibiting the positive sign, the cell identification information obtained via green fluorescent live cell staining and red fluorescent biomarker is simultaneously measured. Similarly, with the time series waveform exhibiting the negative sign, the cell identification information obtained via green fluorescent live cell staining and red fluorescent biomarker is simultaneously measured.

Thus, obtained time series waveforms and the positive or negative cell identification information tagged to the respective time series waveforms are simultaneously measured, and accumulated as the learned model. In the process of establishing the learned model, simultaneously measuring the time series waveform and the cell identification information is necessary regardless of whether the cell is fluorescently stained or not stained.

In the present invention, needless to say, the cell identification information may be identified based on a semi-supervised learning based on unlabeled data not associated with the positive time series waveform and the negative time series waveform, in addition to the supervised learning data based on the learned model formed as described above. For example, this is effective when how to label is only partially known, in the case where it is mostly unknown how to label as cancer cells in the blood.

The invention claimed is:

1. A cell evaluation system comprising:
   physical measurement means that performs a physical measurement by:
     irradiating individual cells in a cell group as a measurement object flowing in a flow passage with either a structured excitation light or a structured illuminating light;
     individually interacting the cells in the cell group with either the excitation light or the illuminating light in time series; and
     mapping optical space information of the cells in time series waveforms of signal strength;
   a database that stores a relevance configured in at least three levels, each of the at least three levels of relevance indicating a degree of relevance between the time series waveforms of signal strength as measurement information measured by the physical measurement means and cell identification information; and
   evaluation means that refers to the relevance stored in the database, and identifies the cell identification information of a newly measured cell by performing an operation of selecting at least one piece of the cell identification information based on the time series waveform of signal strength as the measurement information of the newly measured cell measured via the physical measurement means.

2. The cell evaluation system according to claim 1, wherein:

the database stores a learned model from which at least one piece of the cell identification information is selected based on the time series waveform of signal strength as the measurement information of a cell, and the learned model associates each piece of the cell identification information with a combination of a plurality of the time series waveforms with reference to the relevance configured in the at least three levels.

3. The cell evaluation system according to claim 1, wherein:

the database stores a learned model where learning has been performed with reference to the relevance configured in the at least three levels between a time series waveform of a mixture in which a plurality of pieces of the cell identification information are mixed and each piece of the cell identification information, and the evaluation means performs the evaluation by identifying the cell identification information based on measurement information a the mixture having been newly measured via the physical measurement means.

4. The cell evaluation system according to claim 3, wherein:

the database stores a learned model in which a positive time series waveform indicating a higher probability of corresponding to specific cell identification information and a negative time series waveform indicating a lower probability of corresponding to the specific cell identification information are previously learned with reference to the relevance configured in the at least three levels to determine an association between the time series waveforms and the specific cell identification information, and based on a time series waveform of a mixture having been newly measured via the physical measurement means, the evaluation means, using the learned model, determines a probability that the time series waveform of the mixture corresponds to the specific cell identification information by increasing the probability when the positive time series waveform appears in the time series waveform of the mixture, and decreasing the probability when the negative time series waveform appears in the time series waveform of the mixture.

5. The cell evaluation system according to claim 4, wherein:

the database stores the learned model where the negative time series waveform is previously learned with reference to the relevance configured in the at least three levels to identify cell identification information that should be detected, and the evaluation means identifies a piece of cell identification information not corresponding to the negative time series waveform as the cell identification information that should be detected based on the time series waveform of the mixture having been newly measured via the physical measurement means.

6. The cell evaluation system according to claim 1, wherein the relevance is configured as one of a model that is updatable through machine learning, a neural network, and a network that assumes deep learning.

7. The cell evaluation system according to claim 1, wherein the time series waveform of the signal strength as the measurement information is measured by the physical measuring means with one of an electromagnetic wave, a fluorescence, a phase, transmission, a spectrum, multicolor, scattering, reflection, Coherent Raman, Raman or absorption/scattering/transmission/a fluorescence spectrum, a sound, terahertz, and impedance.

8. The cell evaluation system according to claim 1, wherein the individual cells in the cell group as the measurement object flowing in the flow passage are irradiated with either the structured excitation light or the structured illuminating light by emitting either the excitation light or the illuminating light via a specific shading pattern.

9. A cell evaluation method comprising:

performing a physical measurement by irradiating individual cells in a cell group as a measurement object flowing in a flow passage with either a structured excitation light or a structured illuminating light, individually interacting the cells in the cell group with either the excitation light or the illuminating light in time series, and mapping optical space information of the cells in time series waveforms of signal strength;

storing, in a database, a relevance configured in at least three levels, each of the at least three levels of relevance indicating a degree of relevance between the time series waveforms of signal strength as measurement information measured by performing the physical measurement and cell identification information; and performing an evaluation by referring to the relevance stored in the database, and identifying the cell identification information of a newly measured cell by performing an operation of selecting at least one piece of the cell identification information based on the time series waveform of signal strength as the measurement information of the newly measured cell measured by performing the physical measurement.

10. A non-transitory computer-readable recording medium storing a program that is executable by a computer to control the computer to execute processes comprising:

performing a physical measurement by irradiating individual cells in a cell group as a measurement object flowing in a flow passage with either a structured excitation light or a structured illuminating light, individually interacting the cells in the cell group with either the excitation light or the illuminating light in time series, and mapping optical space information of the cells in time series waveforms of signal strength storing, in a database, a relevance configured in at least three levels, each of the at least three levels of relevance indicating a degree of relevance between the time series waveforms of signal strength as measurement information measured by performing the physical measurement and cell identification information; and performing an evaluation by referring to the relevance stored in the database, and identifying the cell identification information of a newly measured cell by performing an operation of selecting at least one piece of the cell identification information based on the time series waveform of signal strength as the measurement information of the newly measured cell measured by performing the physical measurement.

\* \* \* \* \*